United States Patent
Fischer

(10) Patent No.: US 9,138,206 B2
(45) Date of Patent: Sep. 22, 2015

(54) DEVICE FOR TISSUE EXTRACTION

(75) Inventor: Daniel Fischer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 878 days.

(21) Appl. No.: 13/187,720

(22) Filed: Jul. 21, 2011

(65) Prior Publication Data

US 2012/0022401 A1 Jan. 26, 2012

(30) Foreign Application Priority Data

Jul. 21, 2010 (DE) .......................... 10 2010 031 737

(51) Int. Cl.
*A61B 5/05* (2006.01)
*A61B 10/02* (2006.01)
*A61B 17/34* (2006.01)
*A61B 19/00* (2006.01)

(52) U.S. Cl.
CPC ......... *A61B 10/0233* (2013.01); *A61B 17/3403* (2013.01); *A61B 2019/205* (2013.01)

(58) Field of Classification Search
CPC ...... A61B 19/201; A61B 19/00; A61B 10/00; A61B 10/02; A61B 10/0233; A61B 17/3403; A61B 17/3405; A61B 17/3409; A61B 2010/0208
USPC ................... 600/567, 436, 407, 439; 606/130
See application file for complete search history.

(56) References Cited

U.S. PATENT DOCUMENTS

| | | | | |
|---|---|---|---|---|
| 4,727,565 A | * | 2/1988 | Ericson | 378/205 |
| 5,129,911 A | * | 7/1992 | Siczek et al. | 600/429 |
| 5,219,351 A | * | 6/1993 | Teubner et al. | 606/130 |
| 5,386,447 A | * | 1/1995 | Siczek | 378/37 |
| 5,409,497 A | * | 4/1995 | Siczek et al. | 600/407 |
| 5,515,416 A | * | 5/1996 | Siczek et al. | 378/197 |
| 5,855,554 A | * | 1/1999 | Schneider et al. | 600/407 |
| 5,984,930 A | * | 11/1999 | Maciunas et al. | 606/130 |
| 6,050,954 A | * | 4/2000 | Mittermeier | 600/562 |
| 6,198,962 B1 | * | 3/2001 | Su | 600/422 |
| 6,236,880 B1 | * | 5/2001 | Raylman et al. | 600/436 |
| 6,421,454 B1 | * | 7/2002 | Burke et al. | 382/131 |
| 6,468,226 B1 | * | 10/2002 | McIntyre, IV | 600/564 |
| 6,589,254 B2 | * | 7/2003 | Fontenot | 606/130 |
| 6,928,315 B1 | * | 8/2005 | Nachaliel | 600/407 |
| 7,549,424 B2 | * | 6/2009 | Desai | 128/898 |
| 8,335,558 B2 | * | 12/2012 | Manyam et al. | 600/427 |
| 2002/0026127 A1 | * | 2/2002 | Balbierz et al. | 600/567 |
| 2004/0220588 A1 | * | 11/2004 | Kermode et al. | 606/129 |
| 2004/0267121 A1 | * | 12/2004 | Sarvazyan et al. | 600/439 |
| 2008/0045833 A1 | * | 2/2008 | Defreitas et al. | 600/429 |
| 2010/0036245 A1 | * | 2/2010 | Yu et al. | 600/439 |

* cited by examiner

*Primary Examiner* — Rene Towa
(74) *Attorney, Agent, or Firm* — Schiff Hardin LLP

(57) ABSTRACT

In a device for tissue extraction from a breast, a needle mount accommodating a biopsy needle can be placed by a connection element such that no regions of the breast that are to be examined by x-rays are occluded by parts of the device during an x-ray image acquisition.

8 Claims, 2 Drawing Sheets

DEVICE FOR TISSUE EXTRACTION

BACKGROUND OF THE INVENTION

1. Field of the Invention

The present invention relates to devices for extracting a tissue sample from a subject, such as for implementing a biopsy of a breast.

2. Description of the Prior Art

In a biopsy a tissue sample is extracted—for example from the tissue of a breast of a patient—for histological examination. The extraction of the tissue sample can take place with the assistance of imaging methods. An overview volume set of the breast is created with a tomosynthesis method. X-ray images of the breast are acquired to create the overview volume set. For x-ray image acquisition, an x-ray tube is moved (for example in an orbit) over a detector. For example, in a tomosynthesis procedure the x-ray tube moves in an angle range from +25° to −25°. An x-ray radiation in the x-ray source is then triggered at regular intervals, and the respective x-ray image is read out and buffered by the detector. An overview volume set is subsequently created from the multiple projections that are present in digital image data. Regions for the extraction of a tissue sample are localized in the overview volume set, and from this the coordinates are determined for the entry position, direction and depth of a biopsy needle. The biopsy needle is introduced into the breast for tissue extraction. Since an exact fixing of the breast between the detector and a compression plate can be maintained only with great difficulty over the entire examination duration, and the tissue variation to be removed is often only a few cubic millimeters in size, a control volume set with a biopsy needle introduced into the breast tissue is created before the extraction of the tissue sample. The alignment and the position of the biopsy needle tip can be checked by means of the data from the control volume set, and an adaptation and alignment of the biopsy needle can be conducted. However, the arrangement entails the disadvantage that parts of the biopsy unit occlude x-ray image information and generate additional artifacts, known as out-of-plane artifacts.

SUMMARY OF THE INVENTION

An object of the invention is to provide an arrangement for tissue extraction that overcomes the aforementioned disadvantages.

This device for tissue extraction has an alignment unit, a needle mount accommodating at least one biopsy needle and a connection unit. The connection unit is fashioned such that the needle mount can be arranged to the side of a subject. The connection unit is connected via an alignment arm with the alignment unit and can be positioned by means of this, among other things. The connection unit can be displaced vertically and/or horizontally with the alignment arm of the alignment unit. In one embodiment, the connection unit can be fashioned as one piece. The alignment unit is arranged in a boundary region of the detector unit. The needle mount for tissue extraction can be arranged along a circle segment around the subject to be biopsied. The needle mount can be aligned in that the biopsy needle integrated into this can be arbitrarily introduced into a subject.

The device has the advantage that a needle mount accommodating at least one biopsy needle for tissue extraction can be aligned via a connection element such that no regions to be examined are occluded by this during an x-ray acquisition.

The invention has the advantage that out-of-plane artifacts are avoided.

The invention also the advantage that the presentation of the breast tissue is clear and distinct.

The invention has the further advantage that the extraction of the tissue sample takes place with minimization of the penetration depth in the subject.

DESCRIPTION OF THE PREFERRED EMBODIMENTS

In the device for tissue extraction according to the invention, the needle mount accommodating the biopsy needle can be placed via a connection element such that no regions to be examined are occluded by parts of the device during an x-ray acquisition.

Figure 1:
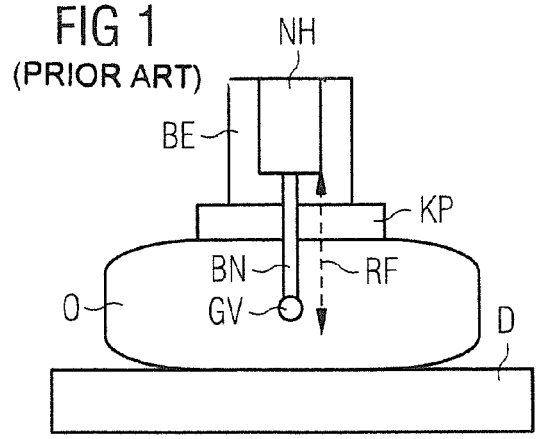
FIG. 1 is a front view of a known biopsy unit.
Figure 2:
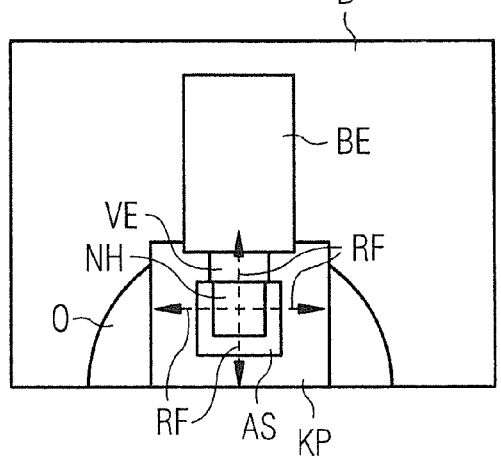
FIG. 2 is a plan view of the biopsy unit of FIG. 1.

FIGS. 1 and 2 show a known biopsy unit BE. With this biopsy unit the biopsy needle is introduced vertically into a breast. The biopsy unit BE is thereby arranged directly above the subject O to be examined. In this known embodiment the subject O is compressed and fixed between compression plate KP and surface of a detector D. For example, this subject O can be the breast of a patient. The breast O remains captive from an overview acquisition until the extraction of the tissue in the compression unit of the mammography apparatus. A biopsy needle BN is attached in a biopsy needle mount NH, and this is connected via a connection unit VE with an alignment arm of an alignment unit BE. The biopsy needle tip BN is aligned on a localized tissue variation GV with control signals relayed to the alignment unit BE and adapted by the alignment unit. This tissue variation GV can be localized by means of an image evaluation algorithm from the calculated slice images from the overview volume set, for example. The slice images are created from a first volume set (that is also designated as an overview volume set). The biopsy needle BN is navigated and aligned on a selected tissue variation GV in a computer-controlled manner after a prioritization of the localized tissue variations GV. For this the predominantly vertically aligned biopsy needle BN is aligned on the tissue variation GV within a recess AS in the compression plate KP. In FIG. 1 the biopsy needle BN is introduced into the tissue of the breast O and aligned on a tissue variation GV. The tip of the biopsy needle BN is positioned directly in front of the localized tissue variation GV. Only after a check—for example after creating a second volume set, which can also be designated as a control volume set—is the biopsy needle aligned again in the event that it is necessary. The extraction of the tissue sample from the localize tissue variation GV takes place after this check.

A plan view of a biopsy unit is shown in FIG. 2. Depicted here are the alignment unit BE and the connection unit VE between alignment unit BE and biopsy needle mount NH. The direction arrows RF reflect the movement directions of the biopsy needle mount NH relative to the detector surface. This arrangement entails the disadvantages that, in an x-ray acquisition, the biopsy needle, portions of the biopsy needle mount NG and the connection unit VE itself are imaged in the x-ray image, and x-ray image information is not made accessible to the observer. The articles additionally generate artifacts in the imaging of a volume set.

Figure 3:
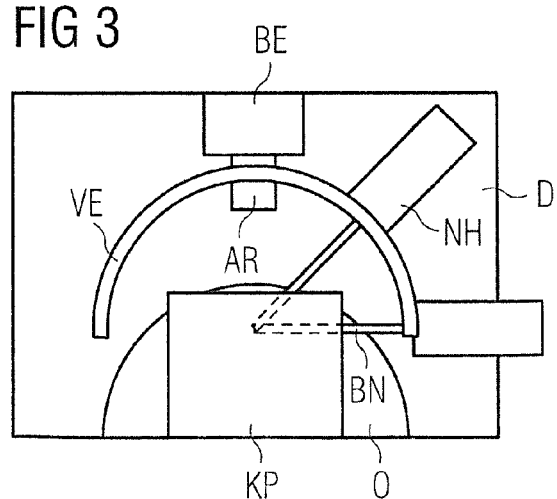
FIG. 3 is a plan view of an exemplary embodiment of the device according to the invention.

FIG. 3 reflects an exemplary embodiment according to the invention. In this embodiment the biopsy needle mount is connected via an arc-shaped connection element VE with an arm AR of the alignment unit BE. In contrast to the arrangement shown in FIGS. 1 and 2, the alignment unit BE is arranged offset from the compression plate KP and the subject to be examined. The needle mount NH can be positioned arbitrarily at the breast by the arc-shaped connection unit VE. Corresponding to the localization of the tissue variation, the biopsy needle mount can be raised or lowered with the arm AR of the alignment unit BE. An optimal initial position for a tissue extraction can be set via the displacement of the biopsy needle mount NH along the arc-shaped connection element VE. For example, the arc-shaped embodiment can also be achieved via multiple elements to be connected with one another in the form of an N-sided polygon. The elements can be fashioned in a straight line. The connection element VE can be attached at the arm AR of the alignment unit BE such that said connection element VE can be displaced. Furthermore, upon displacement of the biopsy needle mount BN along the annulus the tip of the biopsy needle can remain aligned on an isocenter. If an end position is found, the needle mount NG is arrested. A fine alignment can additionally still take place with the alignment unit BE after being stopped. Through this alignment the biopsy needle tip can be aligned exactly on a prioritized tissue variation without the without the possible additional tissue variations being affected by the biopsy needle in the biopsy extraction. As indicated above, the annulus can likewise be raised or lowered by the arm AR of the alignment unit BE. The embodiment has the advantage that no tissue of the breast is occluded by the attachment unit BE and the biopsy needle mount NH in x-ray acquisitions.

Figure 4:
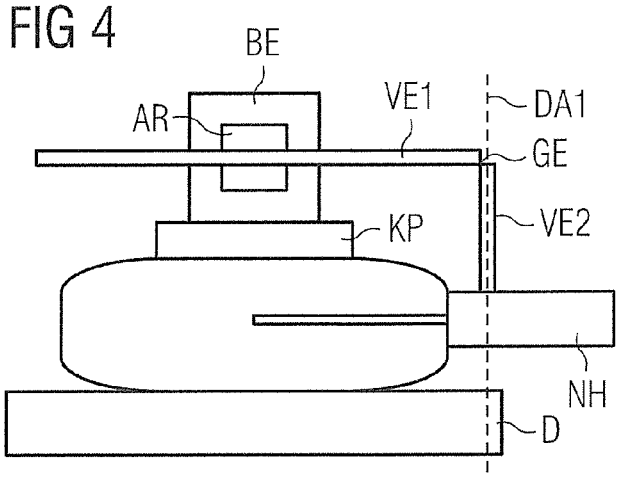
FIG. 4 is a side view of the device of FIG. 3.

FIG. 4 shows a side view of the device shown in FIG. 3. First and second connection elements VE1, VE2 of the connection unit VE are shown in this depiction. The first connection element VE is fashioned in the shape of a semicircle. The two elements are connected by arrestable connection elements, for example joints. In order to raise a biopsy needle aligned parallel to the surface of the detector unit D, either the arm AR controllable by the alignment unit BE or the second connection element VE2 (aligned vertically as shown in this depiction) can be displaced vertically.

Figure 5:
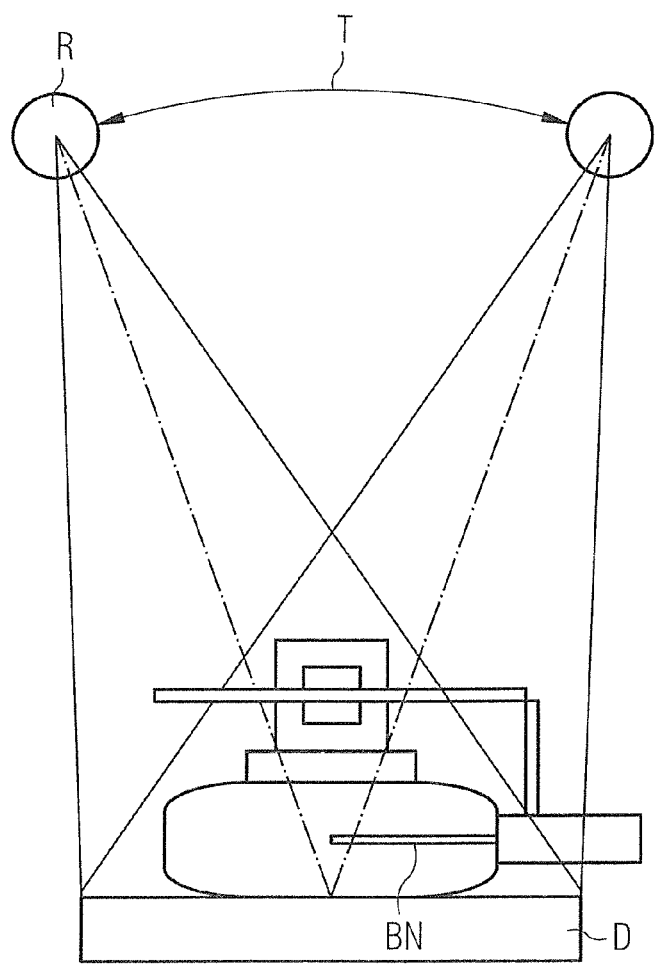
FIG. 5 illustrates a trajectory of an x-ray tube associated with the device according to the invention.

A trajectory T of an x-ray tube R of a mammography apparatus (not shown in detail here) with an adjustment and mounting device for a biopsy needle BN is rendered in FIG. 5. The trajectory T can take place as shown along a circle segment or within a plane. A first sequence—for example of 25 x-ray images—is created for a tomosynthesis. The x-ray tube R is thereby moved across the detector D along a circle segment in an angle range between 25° and −25°. Subjects of different height in the breast are projected differently at different angles. Conspicuous tissue structures in the breast are emphasized by suitable filtering, displacement and summation during the subsequent reconstruction, for example via the methods of filtered back projection. The reconstruction leads to a number of slice images in different depth layers parallel to the detector surface. In the described exemplary embodiment, a first sequence of x-ray images of the compressed breast and a second sequence of x-ray images are produced before a biopsy extraction from the tissue of the breast. A first volume—an overview volume set—is created with the first sequence, and a second volume set—a control volume set—is created with the second sequence. The embodiment and arrangement of the biopsy needle mount has the advantage that no portions of the attachment unit, of the alignment arm, the connection unit or the biopsy needle mount are imaged in the x-ray exposures.

Although modifications and changes may be suggested by those skilled in the art, it is the intention of the inventor to embody within the patent warranted hereon all changes and modifications as reasonably and properly come within the scope of his contribution to the art.

I claim as my invention:

1. In a mammography apparatus comprising a radiation detector comprising a detector surface, an x-ray source that emits an x-ray beam onto said detector surface from a plurality of different directions, thereby producing a plurality of different x-ray projections, said radiation detector comprising exterior detector edges that surround a central area of said detector surface, at which said x-ray projections overlap, and a compression plate disposed above said detector surface and operable to move in a compression direction toward said detector surface in order to compress a breast between said compression plate and said detector surface, the improvement of a tissue extraction device comprising:
   a biopsy needle adapted to extract tissue from said breast;
   a needle mount in which said biopsy needle is received and held;
   an alignment unit situated at one of said exterior edges of said radiation detector, said alignment unit comprising an arm that is moveable parallel to said compression direction to a selected height above said detector surface and beneath said compression plate; and
   a connection unit including a semi-circular member attached to said arm and a second member connected to said semi-circular member and extending parallel to said compression direction, said needle mount being connected to said semi-circular member via said second member, wherein said second member and said needle mount are selectively positionable along said semi-circular connection unit at a plurality of different positions that define a plane at said selected height, with said biopsy needle held in said mount and inserted into said breast to a selected depth in said plane in said breast, wherein said needle mount is moveable parallel to said compression direction along said second member, and
   wherein said semi-circular member includes a radius that maintains said semi-circular member, said second member, and said needle mount outside of said central area in which said x-ray projections overlap.

2. A device as claimed in claim 1, wherein said connection unit is configured to align said plane parallel to said detector surface of said radiation detector.

3. A device as claimed in claim 1, wherein said alignment unit is mounted so as to vertically displace said connection unit.

4. A device as claimed in claim 1, wherein said connection unit is mounted so as to be horizontally displaceable with respect to said alignment unit.

5. A device as claimed in claim 1, wherein said semi-circular member and said second member are connected by an arrestable connection element.

6. A device as claimed in claim 1, wherein said needle mount is rotatable around a rotation axis of said connection unit.

7. A device as claimed in claim 1, comprising a support on which the subject is supported, and wherein said needle mount is alignable parallel to said support.

8. A device as claimed in claim 1, comprising a support on which the subject is supported, and wherein said needle mount is alignable to introduce said biopsy needle at an angle into the subject with respect to said support.

* * * * *